United States Patent
Balaraman et al.

(10) Patent No.: US 9,944,579 B2
(45) Date of Patent: Apr. 17, 2018

(54) CATALYTIC HYDROGENATION PROCESS FOR THE SYNTHESIS OF TERMINAL DIOLS FROM TERMINAL DIALKYL ALIPHATIC ESTERS

(71) Applicant: Council of Scientific & Industrial Research, New Delhi (IN)

(72) Inventors: Ekambaram Balaraman, Maharashtra (IN); Manoj Kumar Sahoo, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/544,243

(22) PCT Filed: Jan. 15, 2016

(86) PCT No.: PCT/IN2016/050013
§ 371 (c)(1),
(2) Date: Jul. 17, 2017

(87) PCT Pub. No.: WO2016/113758
PCT Pub. Date: Jul. 21, 2016

(65) Prior Publication Data
US 2017/0349514 A1     Dec. 7, 2017

(30) Foreign Application Priority Data
Jan. 15, 2015  (IN) .................................. 131/2015

(51) Int. Cl.
C07C 29/136   (2006.01)
C07C 29/149   (2006.01)
B01J 31/00    (2006.01)
B01J 31/22    (2006.01)

(52) U.S. Cl.
CPC ........... *C07C 29/149* (2013.01); *B01J 31/226* (2013.01); *B01J 2231/641* (2013.01); *B01J 2531/0258* (2013.01); *B01J 2531/821* (2013.01)

(58) Field of Classification Search
CPC ..... C07C 29/136; C07C 29/149; B01J 31/226
USPC ....................................................... 568/864
See application file for complete search history.

(56) References Cited

U.S. PATENT DOCUMENTS

| | | | |
|---|---|---|---|
| 3,314,987 A | 4/1967 | Case | |
| 4,751,334 A | 6/1988 | Turner et al. | |
| 5,030,771 A | 7/1991 | Fuhrmann et al. | |
| 5,406,004 A | 4/1995 | Eastland et al. | |
| 6,232,511 B1 | 5/2001 | Haas et al. | |
| 6,844,452 B2 | 1/2005 | Wood et al. | |
| 8,471,048 B2 | 6/2013 | Kuriyama et al. | |
| 8,846,983 B2 | 9/2014 | Hori et al. | |
| 2015/0329455 A1 | 11/2015 | Ootsuka et al. | |

FOREIGN PATENT DOCUMENTS

WO   WO 2006/106484 A1   10/2006
WO   WO 2014/036650 A1   3/2014

OTHER PUBLICATIONS

Ahmadi et al. 2011 "High Productive Ethylene Trimerization Catalyst Based on CrCl3/SNS Ligands" *Catalysis Letters* 141(8): 1191-1198.
Balaraman et al. 2012 "Efficient hydrogenation of biomass-derived cyclic di-esters to 1,2-diols" *Chem Commun* 48: 1111-1113.
Bertoli et al. 2011 "Osmium and Ruthenium Catalysts for Dehydrogenation of Alcohols" *Organometallics* 30(13): 3479-3482.
Fairweather et al. 2015 "Homogeneous hydrogenation of fatty acid methyl esters and natural oils under neat conditions" *Organometallics* 34(1): 335-339.
Fogler et al. 2011 New CNN-Type Ruthenium Pincer NHC Complexes. Mild, Efficient Catalytic Hydrogenation of Esters Organometallics, 2011, 30 (14), pp. 3826-3833.
Gunanathan 2014 "Bond Activation and Catalysis by Ruthenium Pincer Complexes" by C Gunanathan et al. published *Chem Rev* 114(24): 12024-12087.
Hanton et al. 2011 "Ruthenium-catalyzed hydrogenation of esters using tripodal phosphine ligands" *Journal of Molecular Catalysis A: Chemical* 346(1-2): 70-78.
Kuriyama et al. 2012 "Catalytic Hydrogenation of Esters. Development of an Efficient Catalyst and Processes for Synthesizing (R)-1,2-Propanediol and 2-(l-Menthoxy)ethanol" *Org. Process Res. Dev.* 16(1): 166-171.
Santos et al. 2004 "Hydrogenation of dimethyl adipate over bimetallic catalysts" *Catalysis Communications* 5(7): 377-381.
Sun et al. 2011 "Ester hydrogenation catalyzed by Ru-CNN pincer complexes" *Chem Commun* 47: 8349-8351.
Toba et al. 1999 "Synthesis of alcohols and diols by hydrogenation of carboxylic acids and esters over Ru—Sn—Al2O3 catalysts" *Applied Catalysis A: General*, 189(2): 243-250.
Zhang et al. 2011 "Electron-Rich PNP- and PNN-Type Ruthenium(II) Hydrido Borohydride Pincer Complexes. Synthesis, Structure, and Catalytic Dehydrogenation of Alcohols and Hydrogenation of Esters" *Organometallics* 30(21): 5716-5724.
Deshpande, et al. 1990 "Studies on ruthenium-Tin boride catalysts" *Journal of Catalysis* 121(1): 174-182.
Spasyuk, et al. 2013 "Replacing phosphorus with sulfur for the efficient hydrogenation of esters" *Angewandte Chemie International Edition* 52(9): 2538-2542.

*Primary Examiner* — Sikarl A Witherspoon
(74) *Attorney, Agent, or Firm* — Knobbe, Martens, Olson & Bear, LLP

(57) ABSTRACT

A phosphorus ligand-free, mild, efficient and complete catalytic hydrogenation process is for the sustainable production of terminal diols from renewable terminal dialkyl esters with improved yield. Soluble, phosphorus ligand free Ru (II)-pincer type complexes can be used as catalysts in the hydrogenation process.

9 Claims, No Drawings

CATALYTIC HYDROGENATION PROCESS FOR THE SYNTHESIS OF TERMINAL DIOLS FROM TERMINAL DIALKYL ALIPHATIC ESTERS

FIELD OF THE INVENTION

The present invention relates to a catalytic hydrogenation process for the synthesis of terminal diols from terminal dialkyl aliphatic esters. More particularly, the present invention relates to a single step process for the sustainable production of high value-added specialty chemical 1,3-propanediol (1,3-PDO) from renewable dialkyl malanotes. Further, the present invention relates to novel phosphorus-free soluble Ru (II)-pincer type complexes used as catalyst in hydrogenation process.

BACKGROUND OF THE INVENTION

Aliphatic 1,3-diols, particularly 1,3-propanediol (1,3-PDO), have many applications as monomer units for polyester and polyurethane, and as starting materials for the synthesis various value-added products. 1,3-propanediol was chemically produced either from acrolein or ethylene oxide a petroleum feedstocks. However, as non-renewable crude oil resources become limited, substitutes for petroleum feedstocks are increasingly sought after; as such the synthesis of 1,3-propanediol from renewable resources is of great interest. The non-renewable crude oil resources were used as feedstock chemicals. However, considering the serious concern over the dwindling non-renewable petroleum feedstocks and environmental factors an alternative methods based on renewable resources are of immense interest and highly attractive.

U.S. Pat. No. 5,030,771 disclosed a method of producing aliphatic and cycloaliphatic diols by catalytic hydrogenation of dicarboxylic acid esters under very harsh conditions (higher temperature and higher pressure) by the use of a copper chromite catalyst, wherein said dicarboxylic acid ester has up to 12 carbon atoms in the diacid portion and up to 4 carbon atoms in the alcohol portion.

U.S. Pat. No. 5,406,004 disclosed a process for the production of alcohols and diols by hydrogenation of a corresponding hydrogenatable material selected from monoesters of carboxylic acids, monoesters of dicarboxylic acids, diesters of dicarboxylic acids, lactones, and mixtures of two or more thereof, wherein said catalyst is selected from reduced manganese promoted copper catalysts, reduced copper chromite catalysts, reduced promoted copper chromite catalysts, and chemically mixed copper-titanium catalysts.

Article titled "New CNN-Type Ruthenium Pincer NHC Complexes. Mild, Efficient Catalytic Hydrogenation of Esters" by E Fogler et al. published in *Organometallics*, 2011, 30 (14), pp 3826-3833 reports New pincer ruthenium complexes (2-6) based on the new bipyridine-NHC ligand 1 resulting in an efficient catalytic hydrogenation of esters to the corresponding alcohols under mild conditions. However, this strategy was not applicable to hydrogenation of terminal diesters to terminal diols.

Article titled "Electron-Rich PNP- and PNN-Type Ruthenium(II) Hydrido Borohydride Pincer Complexes. Synthesis, Structure, and Catalytic Dehydrogenation of Alcohols and Hydrogenation of Esters" by J Zhang et al. published in *Organometallics*, 2011, 30 (21), pp 5716-5724 reports Electron-rich phosphorus ligand based PNP- and PNN-type ruthenium(II) hydrido borohydride pincer complexes, [RuH(BH$_4$)($^t$Bu-PNP)] (tBu-PNP=(2,6-bis(di-tert-butylphosphinomethyl)pyridine) (5) and [RuH(BH$_4$)($^t$Bu-PNN)] ($^t$Bu-PNN=2-di-tert-butylphosphinomethyl-6-diethylaminomethylpyridine) (6), were prepared from their corresponding N$_2$-bridged dinuclear Ru(II) complexes [($^t$Bu-PNP)RuCl$_2$]$_2$(μ-N$_2$) (3) and [(R$^t$Bu-PNN)RuCl$_2$]$_2$(μ-N$_2$) (4), respectively. The 6 effectively catalyzes the hydrogenation of nonactivated aromatic and aliphatic esters to the corresponding alcohols with TON~200 under a relatively mild pressure of dihydrogen and neutral and homogeneous conditions.

Article titled "Efficient hydrogenation of biomass-derived cyclic di-esters to 1,2-diols" by E. Balaraman et al. published in *Chem. Commun.*, 2012, 48, 1111-1113 reports an unprecedented homogeneous hydrogenation of cyclic di-esters, in particular biomass-derived glycolide and lactide, to the corresponding 1,2-diols catalyzed by Ru(II) PNN (1) and Ru(II) CNN (2) pincer complexes under mild hydrogen pressure. This strategy is applicable only for cyclic esters (easy to hydrogenate under optimal conditions).

Article titled "Ester hydrogenation catalyzed by Ru—CNN pincer complexes" by Y Sun et al. published in *Chem. Commun.*, 2011, 47, 8349-8351 reports new Ru—CNN pincer catalysts for ester hydrogenation under mild conditions. They synthesized and characterized two new NHC-based CNN-pincer ligands and the corresponding ruthenium (II) complexes 2. Complex 2a can be deprotonated by a strong base to form a 5-coordinate species 3a With dearomatized pyridine moiety in the ligand backbone. Compound 3a can split H$_2$ to form a trans-dihydride species 4a with a rearomatized pyridine moiety in the ligand back-bone.

PCT application no. 2006106484 disclosed a process for the reduction by hydrogenation, using molecular H$_2$, of a C$_3$-C$_7$O substrate containing one or two esters, or lactones, functional groups into the corresponding alcohol, or diol, characterized in that said process is carried out in the presence of a base and at least one catalyst or pre-catalyst in the form of a ruthenium complexes of a tetradentate ligand wherein the coordinating groups consist of at least one amino or imino group and at least one phosphino group.

U.S. Pat. No. 6,232,511 disclosed a process for the production of 1,3-propanediol comprising: hydrogenating an aqueous solution of 3-hydroxypropionaldehyde in the presence of a heterogeneous catalyst, the hydrogenating being carried out at a temperature of from 30° C. to 180° C., a hydrogen pressure of 5 to 300 bar and a pH of from 2.5 to 7.0, wherein the catalyst is a supported catalyst comprising an oxide phase on which ruthenium is disposed in a quantity of from 0.1 to 20 wt %, relative to the oxide phase.

Article titled "catalytic Hydrogenation of Esters. Development of an Efficient Catalyst and Processes for Synthesizing (R)-1,2-Propanediol and 2-(1-Menthoxy)ethanol" by W Kuriyama et al. published in *Org. Process Res. Dev.*, 2012, 16 (1), pp 166-171 reports a ruthenium catalyst for the reduction of esters by hydrogenation to (R)-1,2-propanediol and 2-(1-menthoxy)ethanol.

Article titled "Ruthenium-catalyzed hydrogenation of esters using tripodal phosphine ligands" by M J Hanton et al. published in *Journal of Molecular Catalysis A: Chemical*, 2011, 346 (1-2), pp 70-78 reports the synthesis of a new tripodal phosphine ligand, N(CH$_2$PEt$_2$)$_3$, N-TriPhos$^{Et}$ and the use of tripodal ligands of this type, N(CH$_2$PR$_2$)$_3$ (R=Ph, Et), in conjunction with ruthenium for the catalyzed hydrogenation of dimethyl oxalate (DMO). However complete hydrogenation is difficult.

Article titled "Synthesis of alcohols and diols by hydrogenation of carboxylic acids and esters over Ru—Sn—Al2O3 catalysts" by M Toba et al. published in *Applied Catalysis A: General*, 1999, 189 (2), pp 243-250 reports new sol-gel Ru—Sn—Al$_2$O$_3$ catalysts prepared by a complexing agent-assisted sol-gel method, which selectively hydrogenates unsaturated or aromatic carboxylic acids and their esters to the corresponding unsaturated or aromatic alcohols at low pressure.

Article titled "Hydrogenation of dimethyl adipate over bimetallic catalysts" by SM Santos et al. published in *Catalysis Communications*, 2004, 5 (7), pp 377-381 reports hydrogenation of dimethyl adipate at moderate conditions (5 MPa and 255° C.) aiming at screening the performance of noble metals and some additives on 1,6-hexanediol selective production. Ruthenium was found to be the most active metal and selectively cleavage the O—CH$_3$ bond in the ester group giving the adipic acid monomethyl ester. The production of hexanediol was significant over RuSn/Al$_2$O$_3$ catalyst (49% selectivity).

U.S. Pat. No. 6,844,452 disclosed a process for the co-production of butane-1,4-diol and tetrahydrofuran by hydrogenation of a corresponding hydrogenatable material selected from mono-(C$_1$ to C$_4$ alkyl) esters of dicarboxylic acids, di-(C$_1$ to C$_4$ alkyl) esters of C$_4$ aliphatic dicarboxylic acids, γ-butyrolactone, and mixtures of two or more thereof.

U.S. Pat. No. 3,314,987 disclosed a process for catalytically reducing perfluorinated diesters having the general formula ROOC(CF), COOR, wherein R is a lower alkyl radical, and n is a positive integer having a value of from 2 to 4, inclusive, which process comprises reacting said perfluorinated diester with hydrogen at pressures of from about 8000 to more than 16,000 p.s.i. and temperatures of from about 50-300° C., in the presence of from 20% to 300% by weight, based on the weight of the perfluorinated diester, of a copperchromium oxide catalyst essentially free of uncombined alkaline earth oxide.

U.S. Pat. No. 4,751,334 disclosed a process for the production of butane-1,4-diol by vapor phase hydrogenolysis of a dialkyl ester of a C$_4$ dicarboxylic acid in presence of heterogeneous hydrogenolysis catalyst comprises copper chromite.

U.S. Pat. No. 8,846,983 disclosed a method for reducing a halogenobenzoic acid ester, in which dehalogenation is inhibited in presence of a ruthenium complex represented by the following general formula (1): RuXY(CO)(L)

complex 1

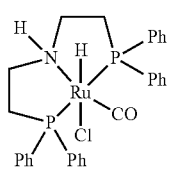

U.S. Pat. No. 8,471,048 disclosed a ruthenium carbonyl complex that is represented by Formula (1): RuXY(CO)(L) (1) wherein X and Y, which may be the same or different from each other, represent an anionic ligand and L represents a tridentate aminodiphosphine ligand represented by Formula (2):

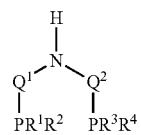

(2)

wherein R$^1$, R$^2$, R$^3$, and R$^4$, which may be the same or different from each other, represent a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, and R$^1$ and R$^2$ or R$^3$ and R$^4$ may bind to each other to form a ring with an adjacent phosphorus atom, the alkyl group, cycloalkyl group, aryl group, aralkyl group, alkyloxy group, cycloalkyloxy group, aryloxy group, aralkyloxy group, heterocyclic group, and substituted amino group may have a substituent group, and Q$^1$ and Q$^2$, which may be the same or different from each other, represent a divalent alkylene group which may have a substituent group, a divalent cycloalkylene group which may have a substituent group, or a divalent aralkylene group which may have a substituent group.

Article titled "Bond Activation and Catalysis by Ruthenium Pincer Complexes" by C Gunanathan et al. published in *Chem. Rev.*, 2014, 114 (24), pp 12024-12087 reports a review on ruthenium pincer complexes of type B (saturated) and C (unsaturated) developed since 2003 from the perspective of bond activation and catalysis.

Article titled "Homogeneous hydrogenation of fatty acid methyl esters and natural oils under neat conditions" by N T Fairweather et al. published in *Organometallics*, 2015, 34 (1), pp 335-339 (Publication Date (Web): Dec. 18, 2014) reports a series of ruthenium- and iron-based pincer catalysts for the homogeneous hydrogenation of fatty acid methyl esters to fatty alcohols with turnover numbers (TONs) of up to 1860. These catalysts operate under neat conditions (no solvent) from the gram to the kilogram scale.

U.S. patent application no. 2015329455 disclosed a process for the production of α,α-difluoroacetaldehyde involves reacting α,α-difluoroacetic acid esters with hydrogen gas (H$_2$) in the presence of a ruthenium catalyst represented by the general formula [2],

[2]

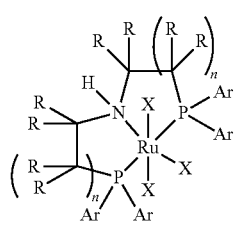

Article titled "Osmium and Ruthenium Catalysts for Dehydrogenation of Alcohols" by M Bertoli et al. published in *Organometallics*, 2011, 30 (13), pp 3479-3482 reports a series of pincer-type complexes of Os and Ru and investigated in catalytic alcohol dehydrogenation. The hydrides OsHCl(CO)[HN(C$_2$H$_4$PiPr$_2$)$_2$] and OsH$_2$(CO)[HN(C$_2$H$_4$PiPr$_2$)$_2$] possess good air, moisture, and thermal stability and are outstanding versatile dehydrogenation catalysts for primary alcohols for reactions of transfer hydrogenation, dehydrogenative coupling, and amine alkylation.

PCT application no. 2014036650 disclosed a novel amino-sulfide metal catalyst for organic chemical syntheses including hydrogenation (reduction) of unsaturated compounds or dehydrogenation of substrates. The range of hydrogenation substrate compounds includes esters, lactones, oils and fats, resulting in alcohols, diols, and triols as reaction products.

Article titled "High Productive Ethylene Trimerization Catalyst Based on $CrCl_3$/SNS Ligands" by E Ahmadi et al. published in *Catalysis Letters*, 2011, 141 (8), pp 1191-1198 reports Methylaluminoxane (MAO)-activated chromium (III) complexes of tridentate SNS ligands of the form $(RSCH_2—CH_2)_2NH$ (R=alkyl, aryl) have been prepared and tested for the trimerization of ethylene to 1-hexene.

Article titled "Replacing Phosphorus with Sulfur for the Efficient Hydrogenation of Esters" by D Spasyuk et al. published in *Angew Chem Int Ed Engl.*, 2013, 52(9), pp 2538-42 reports readily available, air-stable amino-sulfide catalyst, $[RuCl(2)(PPh(3))\{(HN(C(2)H(4)SEt)(2)\}]$. This complex displays outstanding efficiency for the hydrogenation of a broad range of substrates with C=X bonds (esters, ketones, imines), as well as for the acceptorless dehydrogenative coupling of ethanol to ethyl acetate.

The terminal esters are difficult to hydrogenate. The production of terminal diols in one step with improved yield, minimal impurities and by products which requires a catalyst system with good stability both during terminal diols synthesis and during product recovery and recycle. Therefore, it is desirable in the art to identify alternative catalyst systems that demonstrate potential advantages in the one-step production with improved yield of terminal diols.

OBJECTIVE OF THE INVENTION

The main objective of the present invention is to provide a single step phosphorus ligand free catalytic hydrogenation process for the synthesis of terminal diols from terminal dialkyl aliphatic esters.

Another objective of the present invention is to provide a single step process for production of high value-added specialty chemical 1,3-propanediol (1,3-PDO) from renewable dialkyl malanotes.

Yet another objective of present invention is to provide a novel catalyst system comprising a soluble, phosphorus ligand free Ru (II)-pincer type complexes of formula I, II and III for hydrogenation process.

SUMMARY OF THE INVENTION

Accordingly, the present invention provides a single step catalytic hydrogenation process for the synthesis of terminal diols starting from terminal dialkyl aliphatic esters comprises stirring the reaction mixture of phosphorus-free catalyst, potassium tert-butoxide ($^tBuOK$), terminal dialkyl aliphatic esters and toluene at temperature of about 110° C. for the period in the range of 22 to 24 hr under $H_2$ pressure. The yield of said terminal diols is in the range of 35-70%.

In preferred embodiment, said catalyst is selected from $HCl(CO)Ru(^{isoPr}SNS)$ (2), $HCl(CO)Ru(^{Ph}SNS)$ (4) and $HCl(CO)Ru(^{Et}SNS)$ (5).

In another preferred embodiment, said terminal dialkyl aliphatic ester is selected from dialkyl oxalate, dialkyl malonate, dialkyl succinate, diethyl glutarate, dialkyl adipate and said alkyl group may be linear or branched.

In yet another preferred embodiment, said terminal diol is selected from ethane-1,2-diol, propane-1,3-diol, butane-1,4-diol, pentane-1,5-diol, and hexane-1,6-diol. In another embodiment, the present invention provides a phosphorus ligand free catalyst of formula 4;

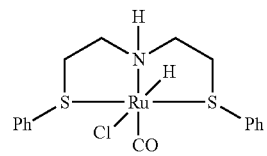

4

In yet another embodiment, the present invention provides a process for the preparation of phosphorus free catalyst of formula 2 and 4 and 5,

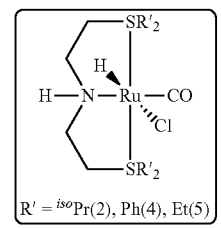

$R' = {}^{iso}Pr(2), Ph(4), Et(5)$ wherein said process comprising the steps of:
a) Adding a methanolic solution of sodium thiolate compound and potassium hydroxide (KOH) to a solution of bis (2-chloroethyl)amine hydrochloride in methanol followed by stirring for 12 to 14 hrs at 30° C. to afford corresponding SNS compound.
b) Refluxing the reaction mixture of compound of step (a), $RuHCl(CO)(PPh_3)_3$ and o-xylene at temperature ranging from 140 to 150° C. for the period ranging from 1 to 2 hr under argon atmosphere to afford desired Ru (II)-pincer type SNS complex.

In another preferred embodiment, said sodium thiolate compound is selected from sodium-2-propanethiolate, sodium thiophenolate (phenyl group may be substituted with other groups) and Sodium ethanethiolate.

In preferred embodiment, said SNS compound is selected from bis(2-(isopropylthio)ethyl)amine [$^{isoPr}SNS$] (1), bis (2-(phenylthio) ethyl) amine [$^{Ph}SNS$] (3) and bis (2-(ethylthio) ethyl) amine [$^{Et}SNS$].

In yet another preferred embodiment, said Ru (II)-pincer type SNS complexes is selected from $HCl(CO)Ru(^{isoPr}SNS)$ (2), $HCl(CO)Ru(^{Ph}SNS)$ (4), and $HCl(CO)Ru(^{Et}SNS)$ (5).

Abbreviations Used 1,3-PDO: 1,3-propanediol

DETAILED DESCRIPTION OF THE INVENTION

The invention will now be described in detail in connection with certain preferred and optional embodiments, so that various aspects thereof may be more fully understood and appreciated.

In the view of above, the present invention provide a single step catalytic hydrogenation process for the synthesis of terminal diols from terminal dialkyl aliphatic esters using a phosphorus free catalyst comprising soluble Ru (II)-pincer type complexes.

In a preferred embodiment, the present invention provides a single step catalytic hydrogenation process for the synthesis of terminal diols starting from terminal dialkyl aliphatic esters comprises stirring the reaction mixture of phosphorus free catalyst, potassium tert-butoxide (ᵗBuOK), terminal dialkyl aliphatic esters and toluene at temperature of about 110° C. for the period in the range of 22-24 hr under H₂ pressure, characterized in that the yield of said terminal diols is in the range of 35-70%.

In preferred embodiment, said phosphorus ligand free catalyst is selected from Ru (II)-pincer type complexes of formula I, II and III.

In preferred embodiment, said catalyst is selected from HCl(CO)Ru($^{iso Pr}$SNS) (2), HCl(CO)Ru($^{Ph}$SNS) (4) and RuHCl(CO)($^{Et}$SNS) (5).

In yet another preferred embodiment, said terminal dialkyl aliphatic ester is selected from dialkyl oxalate, dialkyl malonate, dialkyl succinate, diethyl glutarate, dialkyl adipate and said alkyl group may be linear or branched.

In still another preferred embodiment, said terminal diol is selected from ethane-1,2-diol, propane-1,3-diol, butane-1,4-diol, pentane-1,5-diol, and hexane-1,6-diol.

The one step catalytic hydrogenation process for the synthesis of terminal diols from dialkyl aliphatic esters is as shown in scheme 1 below:

Scheme: 1

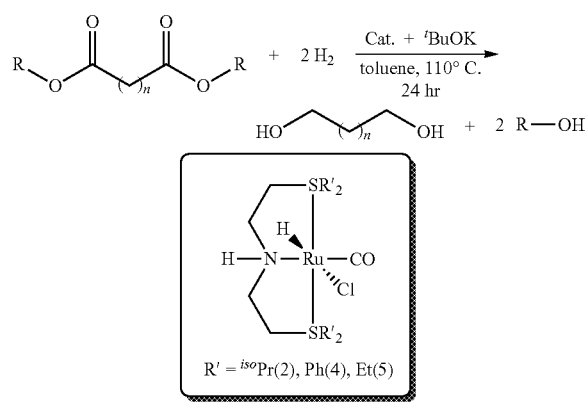

n = 0, 1, 2, 3, 4
R = Me, Et

In another embodiment, the present invention provide a process for the synthesis 1,3-propanediol (1,3-PDO) from renewable dialkyl malanotes. The reaction is catalyzed by a soluble, phosphorus ligand free Ru (II)-pincer type complexes under mild condition (low hydrogen pressure and low temperature).

In another preferred embodiment, the present invention provides a single step catalytic hydrogenation process for the synthesis of 1,3-propanediol (1,3-PDO) starting from renewable dialkyl malanotes comprises stirring the reaction mixture of catalyst, potassium tert-butoxide (ᵗBuOK), dialkyl malanotes and toluene at temperature of about 110° C. for the period in the range of 22-24 hr under H₂ pressure, characterized in that the yield of 1,3-propanediol (1,3-PDO) is 67%.

The process for the synthesis of 1,3-propanediol (1,3-PDO) from renewable dialkyl malanotes is as shown in scheme 2 below:

Scheme 2:

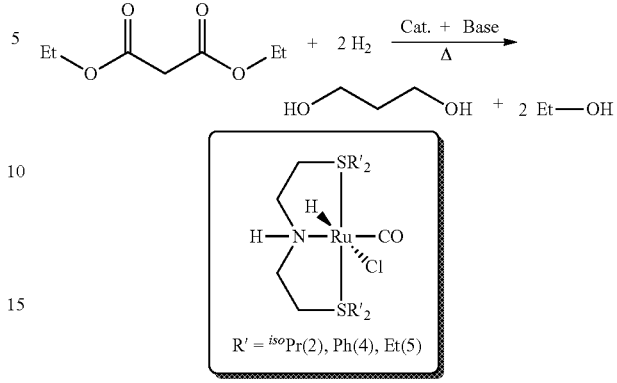

The process yield for the catalytic hydrogenation of diethyl malonate to 1,3-propanediol (1,3-PDO) catalyzed by a soluble, phosphorus ligand free Ru (II)-pincer type complexes at different temperature and pressure is summarized in table 1:

TABLE 1

| Sr. No. | Catalyst | Reaction condition | | | Yield (%)$^a$ |
| --- | --- | --- | --- | --- | --- |
| | | Solvent | Temp. (° C.) | PH₂ (atm) | |
| 1 | 2 | THF | 80 | 4.7 atm | 21 |
| 2 | 2 | toluene | 110 | 4.7 atm | 38 |
| 3 | 2 | toluene | 110 | 6.8 atm | 67 |
| 4 | 4 | toluene | 110 | 6.8 atm | 42 |
| 5 | 5 | toluene | 110 | 6.8 atm | 51 |

$^a$Yield of products (ethanol) were analyzed by GC.

In an embodiment, the present invention provides novel catalysts of formula (I) (II) and (III);

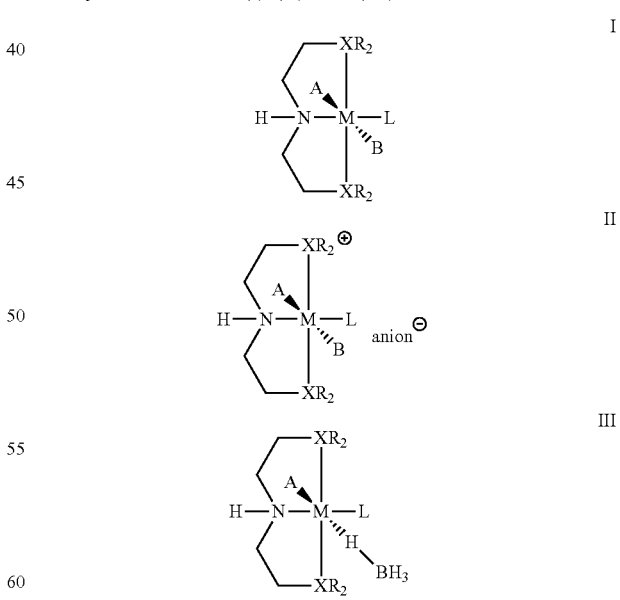

wherein;
M is a noble or transition metal, X is S;
R is isopropyl, ethyl, phenyl (which may be further substituted and selected from the group consisting of alkyl (linear and branched), halogen, trifluromethyl, nitro, amide, ester (—CO$_2$R, —OC(O)R, —OC(O)CF$_3$, —OSO$_2$R, —OSO$_2$CF$_3$) cyano, alkoxy, alkylamino (mono or di), arylamino (mono or di), —SR, an inorganic support and a polymeric moiety) or ethyl. A and B are each independently H or HBH$_3$ or an anionic ligand selected from the group consisting of H, halogen, OCOR$^a$, OCOCF$_3$, OSO$_2$R$^a$, OSO$_2$CF$_3$, CN, OR$^a$, N(R$^a$)$_2$ and R$^a$S.

L is a mono-dentate two-electron donor selected from the group consisting of CO, nitrile (RCN), isonitrile (RNC), N$_2$, CS, heteroaryl, tetrahydrothiophene, alkene and alkyne. R$^a$ is each independently alkyl (linear and branched), cycloalkyl, aryl, heterocyclyl, heteroaryl, alkylcycloalkyl, alkylaryl, alkylheterocyclyl, alkylheteroaryl.

In one embodiment, the present invention provides a phosphorus free catalyst of formula 4;

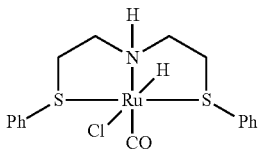

4

In another embodiment, the present invention provides a process for the preparation of phosphorus free catalyst of formula 2 and 4 and 5,

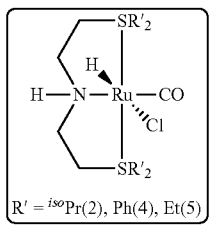

wherein said process comprising the steps of:
a) Adding a methanolic solution of sodium thiolate compound and potassium hydroxide (KOH) to a solution of bis (2-chloroethyl)amine hydrochloride in methanol followed by stirring for 12 to 14 hrs at 30° C. to afford corresponding SNS compound.
b) Refluxing the reaction mixture of compound of step (a), RuHCl(CO)(PPh$_3$)$_3$ (Carbonylchlorohydridotris (triphenylphosphino) ruthenium(II)) and o-xylene at temperature ranging from 140 to 150° C. for the period ranging from 1 to 2 hr under argon atmosphere to afford desired Ru (II)-pincer type SNS complex.

In preferred embodiment, said sodium thiolate compound is selected from sodium-2-propanethiolate, sodium thiophenolate and sodium ethanethiolate.

In another preferred embodiment, said SNS compound is selected from bis(2-(isopropylthio)ethyl)amine [$^{isoPr}$SNS] (1), bis (2-(phenylthio)ethyl)amine [$^{Ph}$SNS] (3) and bis (2-(ethylthio) ethyl) amine [$^{Et}$SNS].

In yet another preferred embodiment, said Ru (II)-pincer type SNS complexes is selected from HCl(CO)Ru($^{isoPr}$SNS) (2), RuHCl(CO)(Ph-SNS) (4), and RuHCl(CO)($^{Et}$SNS) (5).

The following examples, which include preferred embodiments, will serve to illustrate the practice of this invention, it being understood that the particulars shown are by way of example and for purpose of illustrative discussion of preferred embodiments of the invention.

EXAMPLES

Example 1: Hydrogenation of Aliphatic Diesters to Terminal Diols

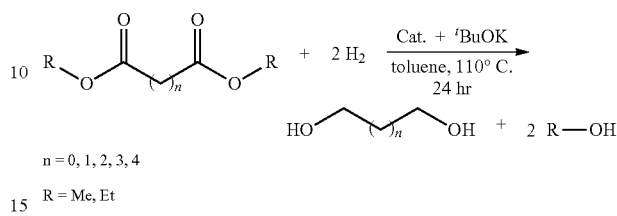

n = 0, 1, 2, 3, 4

R = Me, Et

A 90 mL Fischer-Porter tube was charged under nitrogen with catalyst (0.01 mmol), $^t$BuOK (0.01 mmol), dialkyl esters (1.0 mmol), and toluene (2 mL). The Fischer-Porter tube was purged by three successive cycles of pressurization/venting with H$_2$ (15 psi), then pressurized with H$_2$ (6.8 atm). The solution was heated at 110° C. (bath temperature) with stirring for 24 hr. After cooling to ~5° C. (ice/water), the excess H$_2$ was vented carefully and the products were determined by GC using m-xylene as an internal standard.

The data comprising catalytic hydrogenation of aliphatic diesters to terminal diols is summarized in Table 2.

TABLE 2

| Sr. No | Catalyst | Diester | Products (yield %) |
|---|---|---|---|
| 1 | 2 | Et-O-C(O)-CH$_2$-C(O)-O-Et | HO~~~OH + EtOH (67) |
| 2 | 2 | Me-O-C(O)-CH$_2$-C(O)-O-Me | HO~~~OH + MeOH (62) |
| 3 | 2 | Et-O-C(O)-(CH$_2$)$_2$-C(O)-O-Et | HO~~~~OH + EtOH (69) |
| 4 | 2 | Et-O-C(O)-(CH$_2$)$_3$-C(O)-O-Et | HO~~~~~OH + EtOH (66) |
| 5 | 4 | Et-O-C(O)-(CH$_2$)$_3$-C(O)-O-Et | HO~~~~~OH + EtOH (37) |
| 5 | 5 | Et-O-C(O)-(CH$_2$)$_3$-C(O)-O-Et | HO~~~~~OH + EtOH (49) |

Example 2: Synthesis of 1,3-Propanediol (1,3-PDO)

A 90 mL Fischer-Porter tube was charged under nitrogen with catalyst (0.01 mmol), $^t$BuOK (0.01 mmol), diethyl malonate (1.0 mmol), and solvent (2 mL). The Fischer-Porter tube was purged by three successive cycles of pressurization/venting with H$_2$ (15 psi), then pressurized with H$_2$ (see table 3). The solution was heated at 80 or 110° C. (bath temperature) with stirring for 24 hr. After cooling to ~5° C. (ice/water), the excess H$_2$ was vented carefully and the products were (1,3-PDO and EtOH) determined by GC using m-xylene as an internal standard.

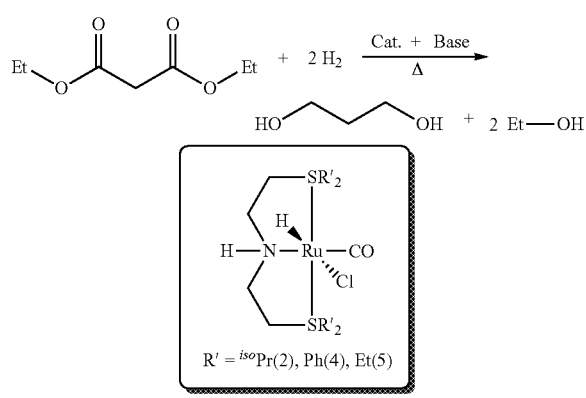

TABLE 3

Catalytic hydrogenation of diethyl malonate to 1,3-propanediol (1,3-PDO).

| | | Reaction condition | | | |
|---|---|---|---|---|---|
| Sr. No. | Catalyst | Solvent | Temp. (° C.) | PH$_2$ (atm) | Yield (%)[a] |
| 1 | 2 | THF | 80 | 4.7 atm | 21 |
| 2 | 2 | toluene | 110 | 4.7 atm | 38 |
| 3 | 2 | toluene | 110 | 6.8 atm | 67 |
| 4 | 4 | toluene | 110 | 6.8 atm | 42 |
| 5 | 5 | toluene | 110 | 6.8 atm | 51 |

[a]Yield of products (ethanol) were analyzed by GC.

Example 3a: Synthesis of $^{isoPr}$SNS (1)

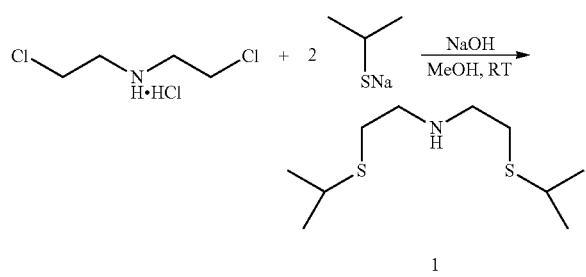

An oven-dried 50 mL round bottom flask equipped with a stirring bar and dropping funnel was cooled under a stream of nitrogen. The flask was then charged with bis(2-chloroethyl)amine hydrochloride (4.46 g, 25.00 mmol) 15 mL of distilled methanol. A methanol solution (20 mL) of sodium-2-propanethiolate (5.45 g, 55.50 mmol) and KOH (30 mmol) was added dropwise during 10 min. Then the mixture was stirred for 12 hrs at 30° C. The solvent was removed under reduced pressure to give yellow slurry and the product was extracted with 3×15 mL of hexane. The combined hexane solutions were removed under vacuum to get oily liquid. This was purified by column chromatography (neutral alumina; petroleum ether:ethyl acetate (20:1) as eluent) to yield 4.54 g (82%) of bis(2-(isopropylthio)ethyl) amine [$^{isoPr}$SNS] (1).

$^1$H NMR (200 MHz, CDCl$_3$): δ 2.87 (m, J=6.0 Hz, 2H, CH), 2.76 (t, J=6.0 Hz, 4H, NHCH$_2$), 2.63 (t, J=6.0 Hz, 4H, SCH$_2$), 1.77 (br s, 1H, NH), 1.22 (d, J=6.0 Hz, 12H, CH$_3$). $^{13}$C{$^1$H} NMR (100 MHz, CDCl$_3$): δ 48.8 (s, 2C, NCH$_2$), 34.8 (s, 2C, CH), 30.8 (s, 2C, SCH$_2$), 23.6 (s, 4C, CH$_3$). HRMS (FAB) Calculated for C$_{10}$H$_{23}$NS$_2$ [MH$^+$]: 222.1350. Found: 222.1345.

Example 3b: Synthesis of HCl(CO)Ru($^{isoPr}$SNS) (2)

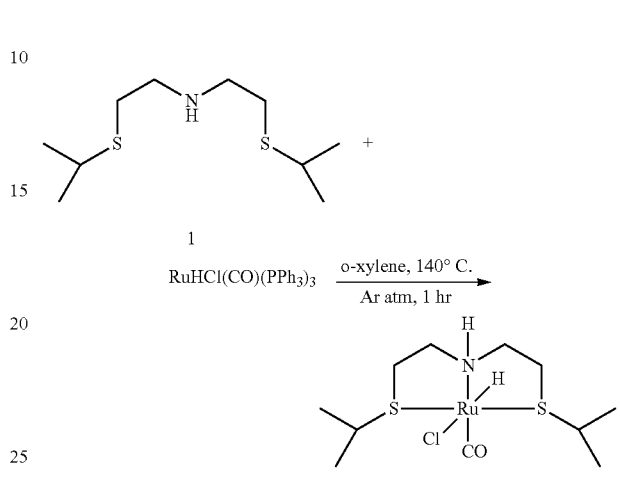

To an oven dried 20 mL schlenk tube equipped with magnetic stirring bar was added bis (2-(isopropylthio) ethyl) amine [$^{isoPr}$SNS] (220 mg, 0.94 mmol), RuHCl(CO)(PPh$_3$)$_3$ (0.85 mmol), and 8 mL dry o-xylene under argon atmosphere. The reaction mixture was refluxed under argon atm in a preheated oil bath maintained at 140° C. for 1 hr, then cooled to room temperature to lead to precipitation of a greenish-yellow solid. The solvent was decanted and the solid thus obtained was washed with ether (3×5 mL), then dried under vacuum to give RuHCl(CO)($^{iso}$Pr—SNS) (210 mg, 54%).

IR (KBr pellet, cm$^{-1}$): 1924, 1960, 3165. $^1$H NMR (200 MHz, CD$_2$Cl$_2$): δ 4.43 (br s, NH), 3.73-3.35 (m, 4H, CH$_2$), 3.08-2.92 (m 2H, CH), 2.87-2.59 (m, 4H, CH$_2$), 1.47-1.36 (m, 12H, CH$_3$), −16.60 (s, 17%, RuH), −17.11 (s, 62%, RuH), −17.65 (s, 21%, RuH). $^{13}$C{$^1$H} NMR (100 MHz, CD$_2$Cl$_2$): a mixture of isomers δ 205.5 (br s, CO), 52.2 and 52.1 (2s, NCH$_2$), 51.2 and 50.9 (2s, NCH$_2$), 43.9 and 43.4 (2s, SCH(CH$_3$)$_2$), 41.4 and 40.7 (2s, SCH(CH$_3$)$_2$), 39.6 and 39.3 (2s, SCH$_2$), 36.6 and 36.7 (2s, SCH$_2$), 21.8 and 21.9 (2s, CH(CH$_3$)$_2$), 21.5 (br s, CH(CH$_3$)$_2$), 21.3 and 21.2 (2s, CH(CH$_3$)$_2$), 21.03 and 20.93 (2s, CH(CH$_3$)$_2$). HRMS (FAB) Calculated for C$_{11}$H$_{24}$NORuS$_2$ [M-Cl]$^+$: 352.0343. Found: 352.0330.

Example 4a: Synthesis of $^{Ph}$SNS (3)

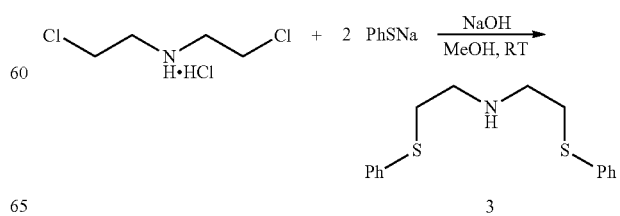

An oven-dried 50 mL round bottom flask equipped with a stirring bar and dropping funnel was cooled under a stream of nitrogen. The flask was then charged with bis (2-chloroethyl)amine hydrochloride (4.46 g, 25.00 mmol) 15 mL of distilled methanol. A methanol solution (20 mL) of sodium thiophenolate (4.77 g, 55.50 mmol) and KOH (30 mmol) was added dropwise during 10 min. Then the mixture was stirred for 12 hrs at 30° C. The solvent was removed under reduced pressure to give yellow slurry and the product was extracted with 3×15 mL of hexane. The combined hexane solutions were removed under vacuum to get oily liquid. This was purified by column chromatography (neutral alumina; petroleum ether:ethyl acetate (20:1) as eluent) to yield 5.86 g (81%) of bis (2-(phenylthio) ethyl) amine[$^{Ph}$SNS] (3).

$^1$H NMR (200 MHz, CDCl$_3$): δ 7.38-7.15 (m, 10H, Phenyl-H), 3.04 (br d, J=8 Hz, 4H, SCH$_2$), 2.83 (br d, J=8 Hz, 4H, NHCH$_2$). $^{13}$C{$^1$H} NMR (100 MHz, CDCl$_3$): δ 135.7 (s, 2C, SCH$_2$), 129.9 (s, 4C, ortho-(C)Ph), 129.1 (s, 4C, meta-(C)Ph), 126.1 (s, 2C, para-(C)Ph), 47.8 (s, 2C, NHCH$_2$), 34.3 (s, 2C, SCH$_2$). HRMS (FAB) Calculated for C$_{16}$H$_{20}$NS$_2$ [MH+]: 290.1037. Found: 290.1032.

Example 4b: Synthesis of HCl(CO)Ru($^{Ph}$SNS) (4)

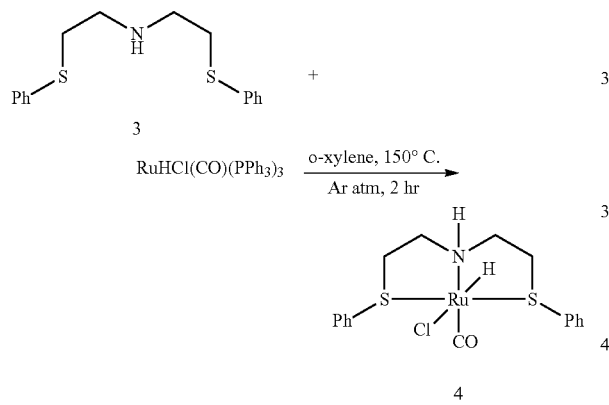

To an oven dried 20 mL schlenk tube equipped with magnetic stirring bar was added bis(2-(phenylthio)ethyl) amine [$^{Ph}$SNS] (272 mg, 0.94 mmol), RuHCl(CO)(PPh$_3$)$_3$ (0.85 mmol), and 8 mL dry o-xylene under argon atmosphere. The reaction mixture was refluxed under argon atm in a preheated oil bath maintained at 150° C. for 2 hr, then cooled to room temperature to form a reddish brown precipitate. The solvent was decanted and the solid thus obtained was washed with ether (3×5 mL), then dried under vacuum to give analytically pure complex RuHCl(CO)($^{Ph}$SNS) (318 mg, 70%).

HRMS (FAB) Calculated for C$_{17}$H$_{20}$NORuS$_2$ [M-Cl]$^+$: 420.0030. Found: 420.0023.

ADVANTAGES OF THE INVENTION

Environmentally benign approach.
Cheap and easily available raw materials used.
Simple and cost-effective process.
Single step process with improved yield.

We claim:

1. A catalytic hydrogenation process for synthesis of terminal diols starting from terminal dialkyl aliphatic esters, comprising, stirring a reaction mixture of phosphorus free catalyst, potassium tert-butoxide ($^t$BuOK), terminal dialkyl aliphatic esters and toluene at temperature of 110° C. for a period in the range of 22 to 24 hr under H$_2$ pressure, wherein said catalyst is selected from the group consisting of HCl (CO)Ru($^{isoPr}$SNS) (2), HCl(CO)Ru($^{Ph}$SNS) (4), and HCl (CO)Ru($^{Et}$SNS) (5), represented by the formula

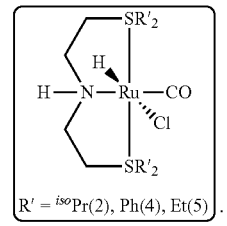

2. The process as claimed in claim 1, wherein said terminal dialkyl aliphatic ester is selected from the group consisting of dialkyl oxalate, dialkyl malonate, dialkyl succinate, diethyl glutarate and dialkyl adipate, wherein alkyl groups in said terminal dialkyl aliphatic ester is linear or branched.

3. The process as claimed in claim 1, wherein said terminal diol is selected from the group consisting of ethane-1,2-diol, propane-1,3-diol, butane-1,4-diol, pentane-1,5-diol, and hexane-1,6-diol.

4. The process as claimed in claim 1, wherein a yield of said terminal diols is in the range of 35-70%.

5. A phosphorus-free catalyst of formula 4:

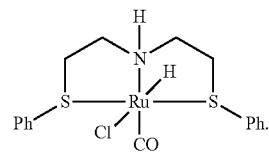

6. A process for the preparation of phosphorus free catalyst selected from the group consisting of HCl (CO)Ru($^{isoPr}$SNS) (2), HCl(CO)Ru($^{Ph}$SNS) (4), and HCl (CO)Ru($^{Et}$SNS) (5), represented by the formula

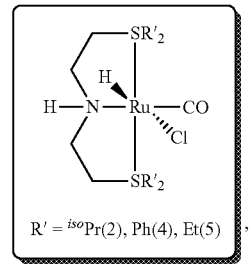

wherein said process comprises:
(a) adding a methanolic solution of sodium thiolate compound and potassium hydroxide (KOH) to a solution of bis (2-chloroethyl)amine hydrochloride in methanol followed by stirring for 12 to 14 hrs at 30° C. to afford corresponding SNS compounds; and
(b) refluxing the reaction mixture of compound of step (a), RuHCl(CO)(PPh$_3$)$_3$ and o-xylene at temperature ranging from 140 to 150° C. for a period ranging from 1 to 2 hr under argon atmosphere to yield Ru (II)-pincer type SNS complexes.

7. The process as claimed in claim 6, wherein said sodium thiolate compound is selected from the group consisting of sodium-2-propanethiolate, sodium thiophenolate and sodium ethanethiolate.

8. The process as claimed in claim 6, wherein said SNS compounds are selected from the group consisting of bis (2-(phenylthio) ethyl) amine [$^{Ph}$SNS] (3), bis(2-(isopropyl-thio)ethyl)amine [$^{isoPr}$SNS] (1) and bis (2-(ethylthio) ethyl) amine [$^{Et}$SNS].

9. The process as claimed in claim 6, wherein said Ru (II)-pincer type SNS complexes is selected from the group consisting of HCl(CO)Ru($^{isoPr}$SNS) (2), HCl(CO)Ru($^{Ph}$-SNS) (4), and HCl(CO)Ru(Et-SNS) (5).

* * * * *